(12) United States Patent
Kritzman et al.

(10) Patent No.: US 6,921,647 B2
(45) Date of Patent: *Jul. 26, 2005

(54) SECRETION-MONITORING ARTICLE

(75) Inventors: Amnon Kritzman, Zichron Yaakov (IL); Nitsa G. Nachshon, Kibbutz Geva (IL); Bechar Yael, Moshav Ein Ayala (IL)

(73) Assignee: Common Sense Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/285,499

(22) Filed: Nov. 1, 2002

(65) Prior Publication Data

US 2003/0166293 A1 Sep. 4, 2003

Related U.S. Application Data

(63) Continuation-in-part of application No. PCT/IL02/00588, filed on Jul. 18, 2002, which is a continuation-in-part of application No. 09/907,926, filed on Jul. 19, 2001, now Pat. No. 6,627,394.
(60) Provisional application No. 60/365,684, filed on Mar. 18, 2002.

(51) Int. Cl.[7] .................................................. C12Q 1/58
(52) U.S. Cl. ......................................... 435/12; 422/56
(58) Field of Search .................. 435/4, 12; 422/56–60; 436/111, 169; 600/573, 584; 604/358

(56) References Cited

U.S. PATENT DOCUMENTS

| 2,664,879 A | 1/1954 | Hardy ............................ 128/2 |
| 3,427,225 A | 2/1969 | Harvill ..................... 195/103.5 |
| 3,509,872 A | 5/1970 | Truhan ........................... 128/2 |
| 4,029,597 A | 6/1977 | Neisius et al. ............... 252/408 |
| 4,029,598 A | 6/1977 | Neisius et al. ............... 252/408 |
| 4,532,216 A | 7/1985 | Wang ............................ 436/2 |
| 4,666,833 A | 5/1987 | Roy et al. ...................... 435/26 |
| 5,063,930 A | 11/1991 | Nucci ........................... 128/632 |
| 5,094,955 A | 3/1992 | Calandra et al. ............. 435/291 |
| 5,217,444 A | 6/1993 | Schoenfeld ................. 604/361 |
| 5,275,591 A | 1/1994 | Mavinkurve ................. 604/387 |
| 5,312,591 A | 5/1994 | Doi ............................. 422/56 |
| 5,384,411 A | 1/1995 | Robotti et al. ................ 549/31 |
| 5,425,377 A | 6/1995 | Caillouette ................... 128/759 |
| 5,445,147 A | 8/1995 | Schoendorfer et al. ..... 128/632 |
| 5,468,236 A | * 11/1995 | Everhart et al. ............ 604/361 |
| 5,660,790 A | 8/1997 | Lawrence et al. ............ 422/56 |
| 5,823,953 A | 10/1998 | Roskin et al. .............. 600/367 |
| 5,823,954 A | * 10/1998 | Chaffringeon .............. 600/367 |
| 5,853,669 A | 12/1998 | Wolfbeis ................. 424/82.05 |
| 5,876,389 A | 3/1999 | Bouchard et al. ........ 604/385.1 |
| 5,897,834 A | * 4/1999 | Lawrence et al. ............ 422/56 |
| 5,910,447 A | 6/1999 | Lawrence et al. .......... 436/111 |
| 6,099,801 A | 8/2000 | Lawrence et al. ............ 422/56 |
| 6,106,461 A | 8/2000 | Roskin et al. .............. 600/309 |
| 6,126,597 A | 10/2000 | Smith et al. ................ 600/362 |
| 6,149,590 A | * 11/2000 | Smith et al. ................ 600/367 |
| 6,200,817 B1 | 3/2001 | Lawrence ................... 436/111 |
| 6,203,496 B1 | 3/2001 | Gael et al. .................. 600/362 |
| 6,395,955 B1 | 5/2002 | Roe et al. ................... 604/361 |
| 6,426,227 B1 | * 7/2002 | Kritzman et al. ............. 436/43 |
| 6,610,904 B1 | 8/2003 | Thomas et al. ............. 604/383 |
| 6,627,394 B2 | * 9/2003 | Kritzman et al. .............. 435/4 |
| 6,627,790 B2 | 9/2003 | Bouchard et al. ........... 604/383 |
| 6,689,114 B2 | 2/2004 | Bouchard et al. ...... 604/385.14 |
| 2001/0025140 A1 | 9/2001 | Torok et al. ................ 600/367 |

FOREIGN PATENT DOCUMENTS

| DE | 199 14 037 A1 | * | 9/2000 |
| DE | 100 16 383 A1 | * | 6/2001 |

\* cited by examiner

*Primary Examiner*—Ralph Gitomer
(74) *Attorney, Agent, or Firm*—Winston & Strawn LLP

(57) ABSTRACT

A secretion-monitoring article for identifying a secreted biological fluid having a body with an absorbent material and least one pH determining member and a reagent associated with the absorbent material is disclosed. The article can be embodied as a swab, gauze, panty shield, hygienic napkin, diaper or interlabial absorbent structure and can be used to indicate the presence of amniotic fluid, or secretions associated with bacterial, parasite, fungal, or yeast infections without giving a false positive result upon exposure to urine. The present invention also teaches a pH indicator mixture and method of attaching the indicator to a substrate for use alone or integrated in an absorbent body and further teaches a method for monitoring the health condition of a person using the secretion-monitoring article.

34 Claims, 9 Drawing Sheets

US 6,921,647 B2

SECRETION-MONITORING ARTICLE

CROSS-REFERENCE TO RELATED APPLICATIONS

This application is a continuation-in-part of the U.S. national stage designation of International Application PCT/IL02/00588, filed Jul. 18, 2002, which in turn is a continuation-in-part of U.S. application Ser. No. 09/907,926, filed Jul. 19, 2001 now U.S. Pat. No. 6,627,394. The International application claims the benefit of U.S. Provisional Application No. 60/365,684, filed Mar. 18, 2002.

TECHNICAL FIELD

The present invention relates to the field of medical diagnostics and more specifically, to an improved identification of secreted biological fluids using a secretion-monitoring article to identify amniotic fluid or secretions associated with bacterial, parasite, fungal, or yeast infections even in the presence of interfering biological fluids. The present invention also relates to improved methods of attaching an indicator to a substrate and methods of preparing and using a secretion-monitoring article to identify a secretion.

BACKGROUND OF THE INVENTION

Many bodily fluids can be readily identified by chemical properties such as pH. One exceptionally useful method of determining the pH of a liquid sample is through the use of an indicator, a chemical compound or combination of compounds, that has a pH dependent color. Well known examples include tea and wine. General details and descriptions of some indicators can be found, for example, in "Indicators," E. Bishop, Pergamon Press, 1972, chapter 3.

Often an indicator is attached to a solid substrate such as paper. A sample of a liquid of which the pH needs to be determined is applied to the substrate. The pH of the liquid is determined by determining the color of the indicator present on the substrate. Depending on how the indicator is attached to the substrate, application of the liquid sample may cause the indicator to leach out of the substrate. Indicator leaching is undesirable and so the indicator is often substantially immobilized on the substrate.

Many medical conditions can be diagnosed by identifying the chemical and physical properties of a vaginal secretion, such as, by identifying the pH of the secretion. A number of devices involving panty shields with pH indicators are known in the art, for example in U.S. Pat. Nos. 5,217,444, 5,823,953 and 6,106,461. These devices can be worn by the user and whenever there is a secretion it is immediately detected by the pH indicator. International patent application WO01/13097, which discloses an indicator bound to a hydrophilic synthetic membrane substrate and a device, such as a panty shield with an indicator bound to hydrophilic synthetic membrane substrate.

A general problem, however, with these pH indicators is that they often provide "false positives" due to changes in pH on drying, interfering biological fluids and repetitive cycles of drying/wetting. Often a vaginal secretion cannot be identified with absolute certainty by an indicator due to the existence of a plurality of fluids collected with a similar pH. The "false positive" readings can be stressful and time consuming to the user. A device that minimizes these "false positive" readings is needed.

False positive readings can be caused, for example, by interfering biological fluids, such as urine. Vaginal secretions of a patient with vaginosis have a pH between 4.7 and 6.5. Because urine of a healthy patient has a pH between 5.0 and 8.0, it is very difficult to diagnose a secretion as arising from vaginosis with a high degree of confidence by just using a pH based indicator test. One solution known in the art is to sample fluid from within the vagina, where urine is not ordinarily found. This is uncomfortable and requires a visit to a health-care professional.

A second example is the identification of amniotic fluid leaking from the vagina of a pregnant woman. During pregnancy amniotic sac integrity may be compromised and a small amount of amniotic fluid may leak out through the cervix and from the vagina. If diagnosed as such, measures such as patient rest or sealing of the amniotic sack using biological glue may be prescribed. If not diagnosed the amniotic sack may later rupture causing abortion of the pregnancy, or require hospitalization of the woman and infant. If the infant is born prematurely, death or severe handicap may be a result. Extended hospitalization of the infant in an incubator is often necessary.

Due to the severe consequences of amniotic fluid leakage, pregnant women undergo severe stress and often go to a health-care professional upon secretion of any liquid from the vicinity of the vagina. The health-care professional looks for the presence of amniotic fluid by checking the pH of the vaginal secretions, amniotic fluid having a pH of between 6.0 and 8.0. Since pregnant women often have urinary incontinence and since urine typically has a pH of between 5.0 and 8.0, if only pH is checked, a false positive result may occur: urine being identified as amniotic fluid. Consequently, it is necessary that such a vaginal secretion be examined using a microscope for the presence of a fern-shaped pattern indicative of amniotic fluid.

As the time between the fluid secretion and the arrival at the health-care professional may be long, there is often no evidence of amniotic fluid upon examination. The secretion may mistakenly be assumed to be urine, often with tragic consequences. On the other hand, the healthcare professional may decide to err on the side of caution, misdiagnosing the secretion of urine as amniotic fluid leading to an unnecessary hospitalization and patient stress.

U.S. Pat. No. 6,126,597 (the '597 patent) and U.S. Pat. No. 6,149,590, (the '590 patent) a continuation-in-part of the '597 patent, are directed to a device in the form of a sanitary napkin with a pH indicator configured to identify the presence of amniotic fluid in a vaginal secretion is disclosed. The '597 and '590 patents are subject to the problem of giving false positive results. The device of the '590 patent address this problem by further including in the device a microscope visualizable slide configured to gather a portion of a vaginal secretion. If the indicator shows the pH corresponding to that of amniotic fluid, the user presents a health-care professional with the slide. The health-care professional examines the slide with the help of a microscope for the typical fern-shaped patterns indicative of the presence of amniotic fluid.

There are a couple of disadvantages associated with this device. First, it requires that the patient visit the health-care professional to distinguish between positive and false-positives and second, a significant amount of time is lost in the having the slide viewed by a professional to determine if amniotic fluid is actually leaking.

U.S. Pat. No. 5,897,834 discloses a device useful in a clinical setting for the differentiation between urine and vaginal secretions associated with vaginosis or urine and amniotic fluid. The device includes the use of indicators with a negatively charged group immobilized to a solid polymer substrate containing quaternary ammonium groups. Further the device includes a gaseous amine-releasing reagent and an amine indicator. The use of the polymer substrate containing quaternary ammonium groups is disclosed to have an advantage of sharpening the pH dependent color transition. However, these polymer substrates have been found to be less useful in non-clinical settings: the indicated pH of dried vaginal secretions is low enough to be misdiagnosed as indicating vaginosis. Thus although the device disclosed in U.S. Pat. No. 5,897,834 is useful in a clinical setting where the health care professional applies the vaginal secretion to the device and observes the color change, if integrated in a patient useable device, such as a panty shield, the device gives abundant false positive results.

There is a need for an indicator system that can differentiate between a specific biological fluid of interest and an interfering biological fluid, such as, urine. Further there is a need for a device that can distinguish between normal vaginal secretions and those associated with amniotic fluid leakage or vaginosis. Further, a system in which false positive results are minimized, while reducing and the amount of time required to get the reliable result is also needed. Such a system is ideally useable by the patient to lead to greater peace of mind and to minimize unnecessary hospital visits. The characteristics of such an indicator system must not change due to long use or as a result of a wetting drying cycle and must distinguish between interfering biological fluids and minimize false positive readings. The present invention now overcomes these problems and satisfies these needs.

SUMMARY OF THE INVENTION

The present invention overcomes the disadvantages of the prior art by the use of an indicator system integrated into various self useable products. Generally, the invention comprises an article that includes an absorbent material for absorbing a biological fluid secreted from a person and an indicator system that has at least one pH determining member and optionally, a reagent for reacting with the biological fluid to alter its pH so that the secretion can be distinguished. The indicator system is associated with an absorbent material such that the biological fluids contact the indicator system so that a reliable indication of the pH of that fluid can be obtained.

The article can be presented to the user in many forms. It is preferable, however, that the article is in the form of a swab, gauze, panty shield, hygienic napkin, a diaper or interlabial absorbent structure. Furthermore, any user, male or female, young or old, can use the article. The particular examples of the invention as presented herein are not intended to limit the scope of the invention, but simply to illustrate and represent the numerous potential forms in which the invention can be used.

Generally, the pH determining member can be anything that can indicate a pH of a fluid. Preferably the pH determining member records or indicates a pH change after coming in contact with the biological fluid and is resistant to change due to long use or wetting and drying cycles. Advantageously, the reagent used in the indicator system is one that reacts with amniotic fluid, a secretion associated with a bacterial, parasite, fungal, or yeast infection, or urine to change its pH.

Preferably, the article has a mounting means for positioning the absorbent body to receive the fluids secreted during the normal activity of the user, such mounting means being, for example, an adhesive strip or other attachment member.

A preferred embodiment is one in which the secretion-monitoring article has a substrate with a first pH indicator in a first area, a second pH indicator in a second area, and a reagent attached to the substrate in the second area, or alternatively a third area. The indicators are selected so that substantial color transitions occur at different pH values. A liquid contacting the substrate interacts with the indicators and the reagent. If the liquid has the pH of a fluid that is to be identified, at least part of the first area undergoes a substantial color change. The liquid may, however, be an interfering fluid with a pH that changes the color of the first indicator. Therefore, in one embodiment, the reagent is selected to react with the interfering fluid (for example), changing the pH of the liquid and consequently substantially changing the color of at least part of the second area. The presence of the second pH indicator acts as a guarantee against false positive results by allowing a calorimetric differentiation of two fluids with a similar pH.

According to another feature of the present invention, the first pH indicator changes color at a substantially lower pH than does the second pH indicator. Usually, the first area is distinct from the second area and the shape of the area can vary and be any geometrical shape, number, letter, icon, word or a combination thereof.

Another non-limiting embodiment of the invention is a secretion-monitoring article wherein the indicator system has at least one pH determining member having a chemical composition that reacts with biological fluids that contain protonated amine cations differently than bodily fluids that do not contain protonated amine cations. Typically, the indicator system is associated with the absorbent material such that the biological fluids contact the indicator system while being worn.

Advantageously, the secretion-monitoring article can be used for the identification of infected urine. In this embodiment the article comprises a body that includes an absorbent material for absorbing urine from a person and an indicator system that has at least one indicator having a chemical composition that reacts with normal urine differently than infected urine. The indicator in this embodiment changes color when contacted by urine, but if the urine is infected the color change of the indicator is nonreversible.

An additional embodiment is one in which the secretion-monitoring article is designed specifically for the identification of bacterially or parasitic infected vaginal secretions. In this embodiment the article comprises a body that includes an absorbent material for absorbing vaginal secretion and an indicator system that has at least one indicator having a chemical composition that reacts with normal or candida vaginal secretions differently than bacterially or parasitic infected vaginal secretions, wherein the indicator changes color when contacted by bacterially or parasitic infected vaginal secretion having a pH level between 4.3 to 5.0 and a buffer capacity lower than normal or candida vaginal secretions.

Another preferred embodiment of the invention comprises an article that includes a pH determining member with a composition that reacts differently to urine than other biological fluids, such as amniotic fluid. The composition of the pH determining member is able to react differently due to certain chemicals that are present in substantial amounts only in urine, and not in the other biological fluids to be identified. The substrate containing the pH determining member is retained in the vicinity of a vaginal area of the person for an extended period to absorb the fluids. After which the article is removed and observed to determine the health condition of the person from which the biological fluid was collected.

There is also included a method for providing an indication of the health condition of a person by providing a substrate to which are attached a first pH indicator in a first area, a second pH indicator in a second area, and a reagent attached to the substrate in the second area, where the color transitions of each of the two indicators occur at a substantially dissimilar pH. A liquid, such as a biological fluid is applied to the substrate and the first and second area is inspected for a change in color indicative of the health condition of the person. According to a feature of the present invention, the substrate is retained in the vicinity of a vaginal area of the person for an extended period of time such as minutes, hours or even longer, to absorb secreted fluids.

According to a further feature of the present invention, the first pH indicator is configured to substantially change color upon contact with amniotic fluid and the second pH indicator is configured to substantially change color upon contact with urine reacting with the reagent. A preferred reagent is urease. Alternatively, the first pH indicator is configured to substantially change color upon contact with vaginal secretions associated with vaginosis and the second pH indicator is configured to substantially change color upon contact with urine reacting with the reagent.

Further, the invention includes a method of attaching an indicator to a substrate. The substrate can be made of many materials, for example, polypropylene, paper or cotton, polyester membranes and can be of many structures including of a membrane, fabric, mesh, gauze, thread, fiber and a sheet. A mixture of pre-formed polymer (such as a cellulose), a plasticizer, a wetting agent, an ion-balance reagent and an indicator (alone or with a reagent such as urease) is prepared. In some cases it is preferable to add a solvent to the mixture. The mixture is applied to a substrate for example by dipping the substrate in the mixture or by spraying or spreading the mixture onto the substrate. The substrate with the applied mixture is allowed to dry. When dry, the indicator is bound to the substrate with the help of the polymer. This method is exceptionally useful when the indicators have a substantially negatively charged functional group such as an acetate or a sulfonate.

There is also provided according to the teachings of the present invention an additional method of making a diagnostic article comprising of the steps of attaching an indicator to a substrate, especially a neutral substrate, by applying a surfactant solution to the substrate and letting it dry, preferably under vacuum, then once the surfactant is dry, an indicator solution or a solution with a reagent is applied to the substrate and allowed to dry, preferably under vacuum, wherein the indicator to be attached to the substrate preferably is a substantially negatively charged functional group with a cationic surfactant is preferably used; and placing the indicator in association with an absorbent body.

BRIEF DESCRIPTION OF THE DRAWINGS

The invention is herein described, by way of example only, with reference to the accompanying drawings.

DETAILED DESCRIPTION OF THE PREFERRED EMBODIMENTS

Figure 1A:
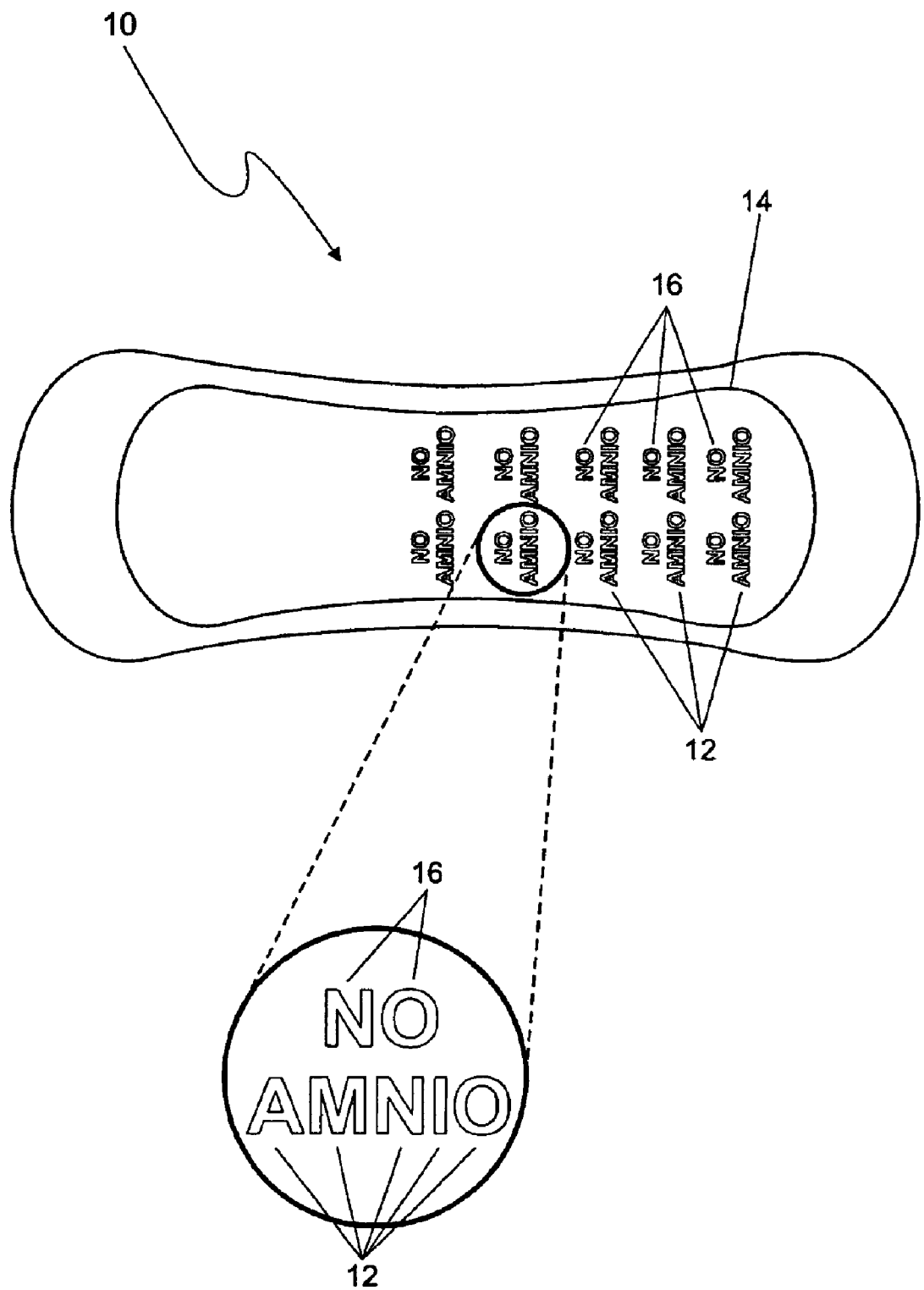
FIGS. 1A–C are schematic top views of an embodiment of the secretion-monitoring article of the present invention with magnification of details of indicators applied to the substrate.

Before turning to details of the present invention, it should be appreciated that the present invention provides secretion-monitoring article and a method for use that allows an untrained user to monitor secreted biological fluids with confidence. The present invention allows for the identification of a specific biological fluid even when there is a possibility for the presence of an interfering biological fluid with a similar pH. The present invention further teaches a pH indicating mixture and method of attaching the mixture to a substrate.

The present invention is an improvement over the prior art, providing a secretion monitoring article that is more reliable and convenient for the user.

In one embodiment of the invention, the secretion-monitoring article comprises a body that includes an absorbent material for absorbing a biological fluid secreted from a person and an indicator system comprising at least one pH determining member and a reagent for reacting with the biological fluid to alter its pH so that the secretion can be distinguished, wherein the indicator system is associated with the absorbent material such that the biological fluids contact the indicator system.

In a second embodiment of the invention, the secretion-monitoring article comprises a body that includes an absorbent material for absorbing a biological fluid secreted from a person and an indicator system comprising a pH determining member that consist of a special composition that reacts with biological fluid differently. One example of such a pH determining member has a special composition that reacts with fluids containing protonated amine cations, such as urine, in a different way than it reacts to other biological fluids that have a low concentration of protonated amine cations, such as amniotic fluid.

In yet another embodiment of the invention, the secretion-monitoring article comprises a body that includes an absorbent material for absorbing a biological fluid secreted from a person and an indicator system comprising a pH determining member that consist of a special composition that reacts with normal urine differently than infected or protein containing urine. In one non-limiting example, the indicator reacts with normal urine (pH 5–8), which changes the color from yellow to green or turquoise. During the drying process the color change of the indicator that has been contacted with normal urine fades as it dries and becomes yellow again. In contrast, when the indicator is contacted by infected or protein containing urine the indicator strip changes color from yellow to green or turquoise and does not fade when dried. Advantageously, this embodiment is well suited for all types of use, for example in pediatrics, geriatrics, and gynecology, and could be presented to the user in many forms, preferably as a diaper or a panty liner.

The secretion-monitoring article can be implemented using many devices and methods. In a preferred embodiment, the article of the present invention is implemented in a manner that can be easily used by non-skilled personnel, specifically a user. The body of the secretion-monitoring article of the present invention comprising the absorbent material can be supplied to the user, for example, in the form of a pad, gauze, a swab, a fiber ball, but most preferably, as a sanitary napkin, diaper, panty shield, and interlabial structure. Details of manufacture of these are well known to one skilled and have been fully described in the prior art, for example U.S. Pat. Nos. 5,217,444, 5,897,834, and 6,149,590.

Furthermore, any user, male or female, young or old, can use the article in a variety of forms. The particular examples of the invention as presented herein are not intended to limit the scope of the invention, but simply to illustrate and represent the numerous potential forms in which the invention can be used.

In one embodiment of the invention, an indicator system made up of a pH determining member and a reagent to be included in the body of the secretion-monitoring article is provided. In another embodiment, an indicator system is made up of pH determining member that reacts differently to different body fluids.

The pH determining member of the indication system can be any pH determining device, for example as a color changing indicator (e.g., litmus paper) or a mobile pH probe. It is preferable, however, that the pH determining member be a color changing indicator, such as a pH determining member made from the pH indicator mixture described herein below and/or using the method of attaching the mixture to a substrate. As will be discussed in more detail below, more than one pH determining member can be part of the indicator system. The pH determining members should be capable of determining substantially different pH ranges or capable of reacting differently to different biological fluids to produce a different color change.

In one embodiment the indicator system comprises a reagent. The reagent is used to distinguish the pH of the biological fluid being monitored from other biological fluids that might interfere with the results and possible give a "false positive" result, with unwarranted stress and expense to the user. The reagent can be chosen based on the biological fluid to be monitored and the type of biological fluids that might interfere with the accurate monitoring of this fluid. The reagent of the indicator system of the present invention is chosen so as to yield reaction products that substantially change the pH of a tested secretion when the tested secretion is either the fluid to be identified or is the interfering fluid, or both. If the reagent is chosen so as to react with both fluids, the pH change resulting from reaction with the fluid to be identified should be different from the pH change resulting from the reaction with the interfering fluid.

In one preferred non-limiting embodiment of the present invention, when either amniotic fluid is to be identified or vaginosis is to be diagnosed, urease (CAS 9002-13-5) is chosen as the reagent. If urine is present, the urine reacts with the urease, releasing ammonia into the tested secretion raising its pH to well above the pH of either amniotic fluid or vaginosis related secretions.

The reagent can also be chosen to react only with the fluid to be identified, change the pH sufficiently to distinguish it from any possible interfering fluid. When the reagent is chosen to only react with the fluid to be identified, it is preferable that the reagent reacts with amniotic fluid or a secretion associated with a bacterial, parasite, fungal, or yeast infection and that the pH is sufficiently changed so as to distinguish the fluid from other possible interfering fluids.

In one embodiment of the invention, the indicator system has only one pH indicator and the reagent is selected to react with the fluid to be identified so that the pH is changed substantial so that the presence of the fluid can easily be identified. In this embodiment of the invention, the pH indicator is selected to indicate the pH of the fluid to be identified after it has reacted with the reagent.

In a preferred embodiments of the secretion-monitoring article, a means for mounting the article to facilitate the collection of the secreted biological fluid is included. An example of a mounting means that is well known in the art is an adhesive strips associated with the article. In a preferred embodiment the article has one or more adhesive strips. The user removes the release tape to expose the adhesive strip of the article and places the article in the crotch portion of their undergarment. This prevents the article from moving out of position during regular use. Types of adhesive compounds that can be used are well know in the art.

Examples of the Secretion-monitoring Articles

The present invention will be exemplified by embodiments of the secretion-monitoring article of the present invention in the form of a panty shield in FIGS. 1–5. The article can be configured to identify amniotic fluid and secretions associated with bacterial, parasite, fungal, or yeast infection, such as infected urine or vaginal secretions. Furthermore, the article is designed to minimize false positive readings associated with interfering biological fluids.

Figure 1B:
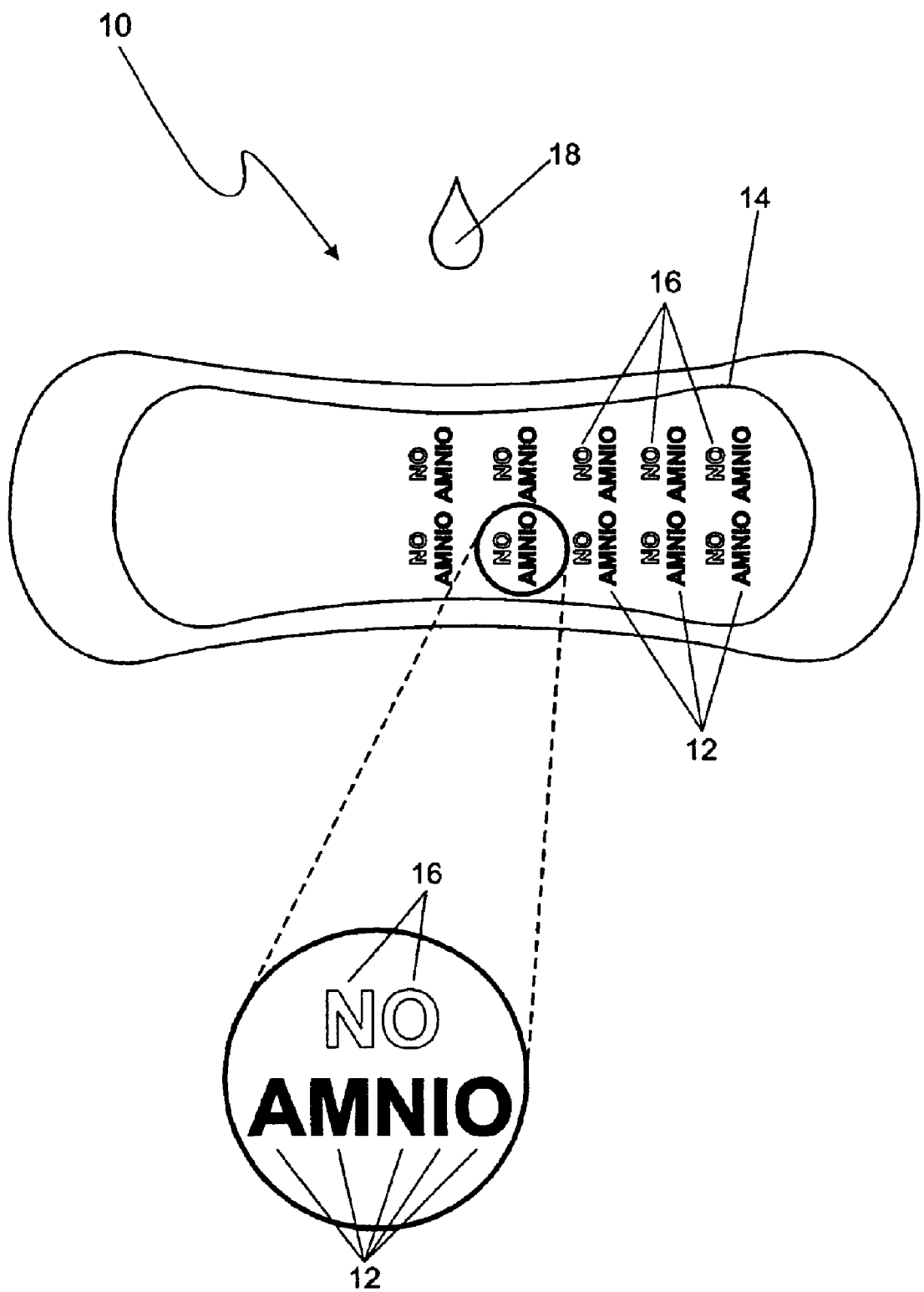
Figure 1C:
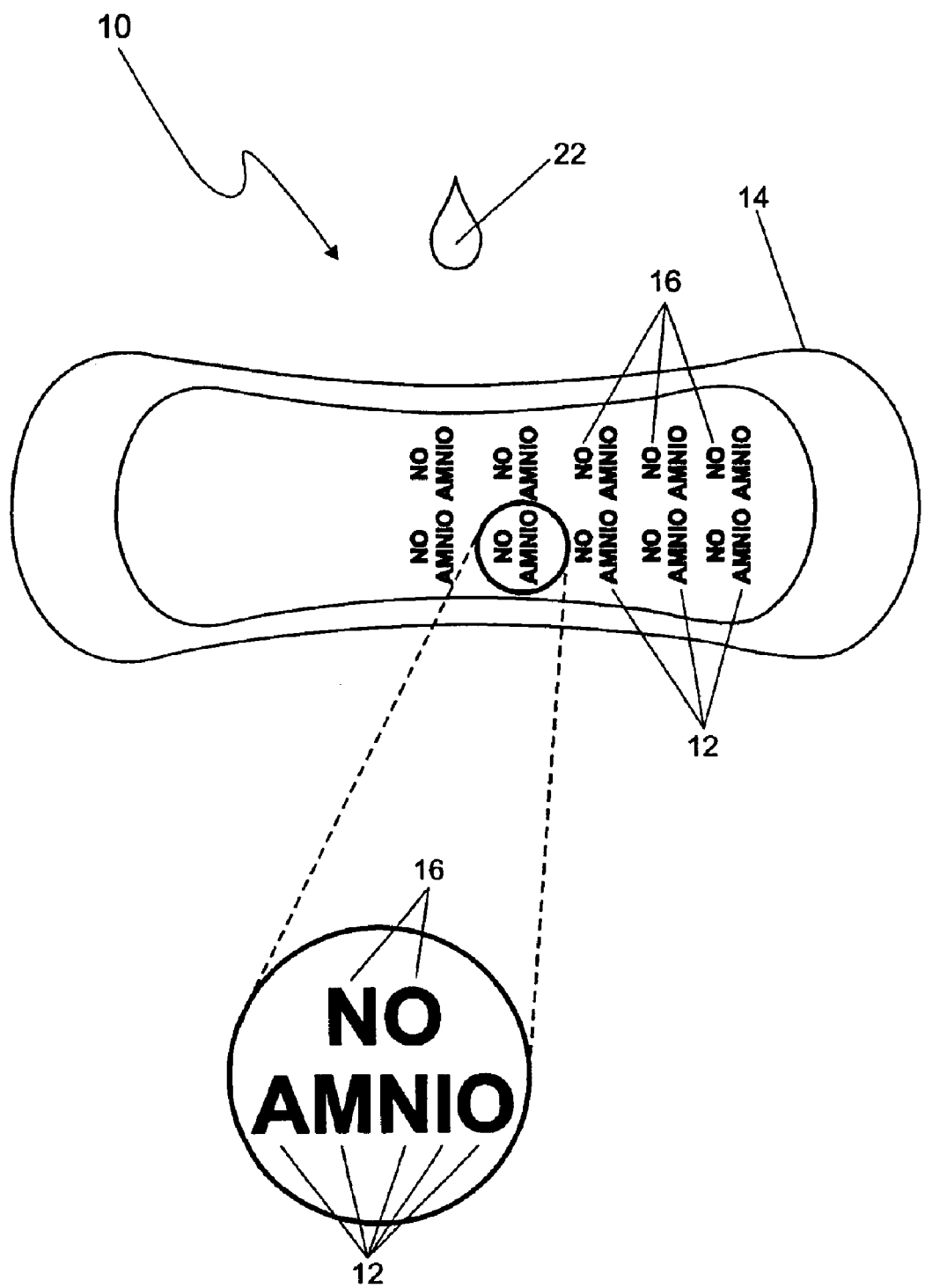
Figure 2:
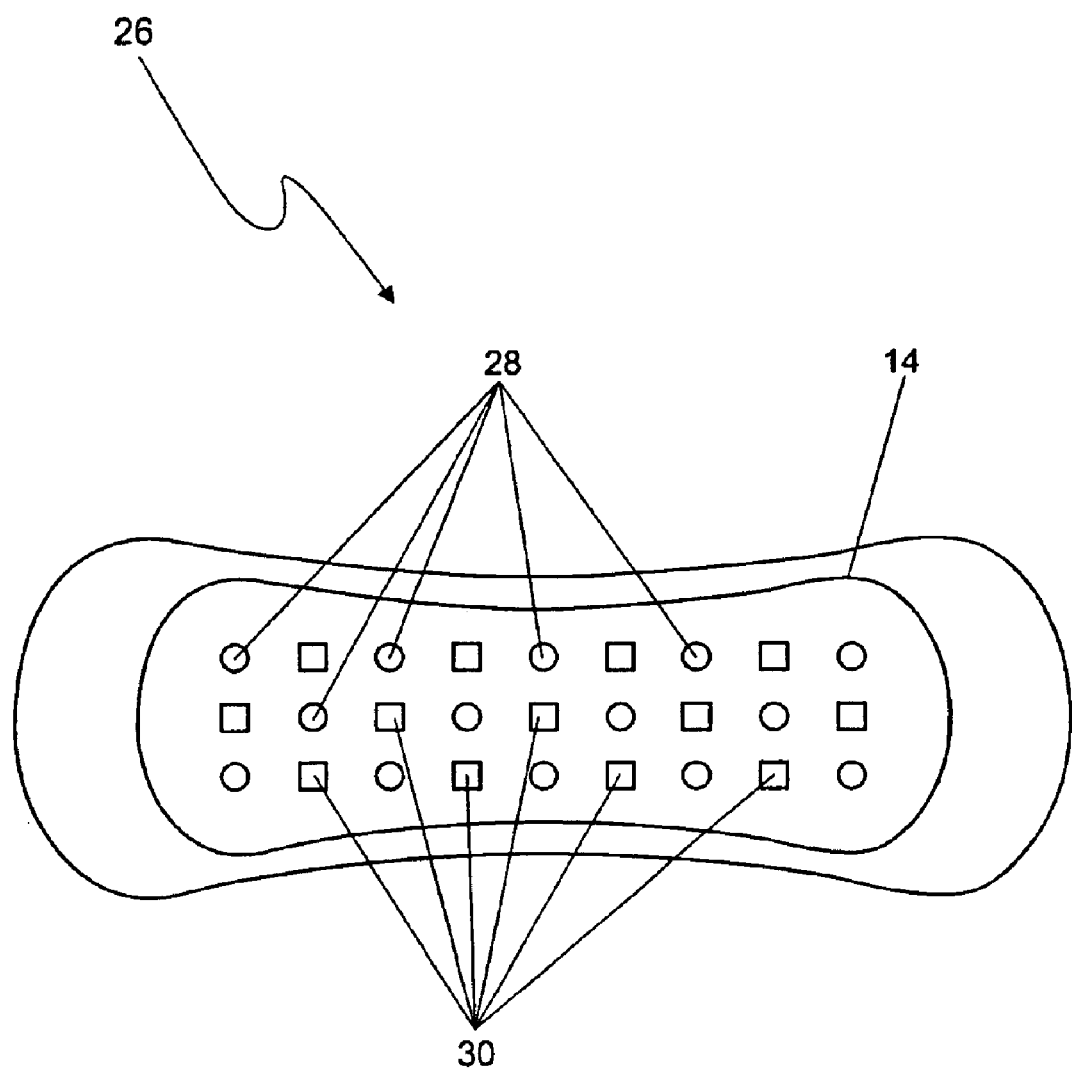
FIG. 2 is a schematic top view of a different embodiment of the secretion-monitoring article of the present invention.
Figure 3:
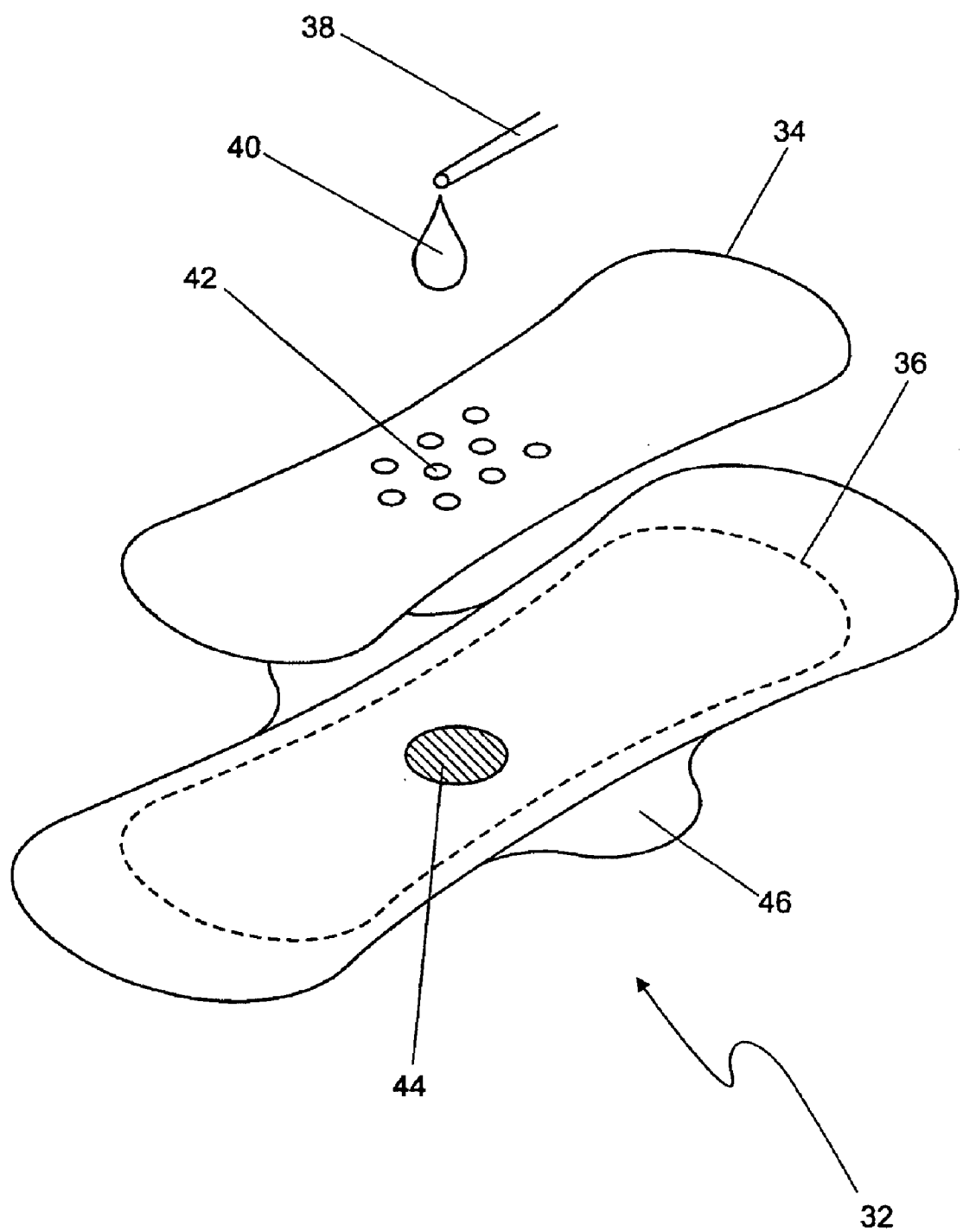
FIG. 3 is a schematic perspective view of a different embodiment of the secretion-monitoring article of the present invention with a microporous membrane.

A preferred embodiment of the invention is one in which the indicator system comprises a first indicator, a second indicator and a reagent. The first indicator of the system of the present invention is chosen so as to identify a first pH. The first pH corresponds to the pH of the fluid that is to be identified. Further, the first pH may also be that of an interfering fluid. When amniotic fluid is to be identified, a first indicator is chosen to indicate that a tested vaginal secretion has a pH of amniotic fluid. Due to the similar pH of urine and amniotic fluid, such a first indicator will also change color when exposed to urine. When vaginosis is to be to diagnosed, a first indicator is chosen to indicate a pH typical of secretions of vaginosis and consequently also of urine. In FIG. 1A, a first indicator is applied at first area 12 on a substrate 14 integrated in a panty shield 10. First area 12 may be arranged as patterns, letters, words or icons, as described in U.S. Pat. No. 5,897,834. In FIGS. 1A–C, first indicator is nitrazine yellow, which is yellow at a pH below 7 and blue violet at a pH above 7.

The reagent of the indicator system of the present invention is chosen so as to yield reaction products that substantially change the pH of a tested secretion as described in detail above.

The second pH indicator of the system of the present invention is chosen so that it indicates the change of pH as a result of the reaction with the reagent. For example, second indicator in FIGS. 1A–C is m-cresol purple m-cresol purple is yellow at a pH of below 7.5 and is violet at a pH above 8.0. The second indicator and the reagent are applied at second area 16 on substrate 14, distinct from the first area 12 on substrate 14, FIG. 1A.

In FIG. 1B, amniotic fluid 18 comes in contact with panty shield 10. Amniotic fluid 18 makes contact with first area 12 and second area 16. As the pH of amniotic fluid 18 is between 7.0 and 7.5, the nitrazine yellow present at first area 12 become blue violet, spelling out the word "AMNIO". It is clear to one skilled in the art that if a small amount of fluid is applied to panty shield 20, it is possible that only part of first area 12 will change color. The m-cresol purple present at second area 16 remains yellow.

When the user of panty shield 20 in FIG. 1B examines panty shield 10, she reads the word "AMNIO" and can go to a health-care professional who can take action corresponding to a high degree of certainty of amniotic fluid secretion.

In FIG. 1C, urine 22 comes in contact with panty shield 10. Urine 22 makes contact with first area 12 and second area 16. As the pH of urine 22 is 7.2, the nitrazine yellow present at first area 12 becomes blue violet, spelling out the word "AMNIO." Urine 20 reacts with urease present at second area 16, releasing ammonia.

The ammonia increases the pH of the liquid present in second area 16 to pH 9. As a result of the high pH, m-cresol purple present at second area 16 becomes violet, spelling out the word "NO."

TABLE 1

| Indicator | aqueous pH transition range | color change | CAS |
|---|---|---|---|
| 1. Cresol Red | 7.2–8.8 | yellow to reddish purple | 1733-12-6 |
| 2. Alizarin | 5.5–6.8 | yellow to violet | 72-48-0 |
| 3. Bromcresol Purple | 5.2–6.8 | yellow to purple | 115-40-2 |
| 4. Chlorophenol Red | 5.2–8.8 | yellow to red | 4430-20-0 |
| 5. Nitrazine Yellow | 6.0–7.2 | yellow to bright blue | 5423-07-4 |
| 6. Bromthymol Blue | 6.0–7.6 | yellow to blue | 34722-90-2 |
| 7. Bromoxylenol Blue | 6.0–7.6 | yellow to blue | 40070-59-5 |
| 8. Neutral Red | 6.8–8.0 | red to yellow | 553-24--9 |
| 9. Phenol Red | 6.8–8.2 | yellow to red | 34487-61-1 |
| 10. Thymol Blue | 8.0–9.2 | yellow to blue | 81012-93-3 |
| 11. Xylenol Blue | 8.0–9.6 | yellow to blue | 125-31-5 |
| 12. m-Cresol purple | 7.4–9.0 | yellow to purple | 2303-01-7 |

When the user of panty shield 24 in FIG. 1C examines panty shield 10, she reads the words "NO AMNIO". The user who became agitated at the unexpected loss of fluid is immediately calmed and is relieved of the necessity of a stressful visit to a health-care professional. It is clear to one skilled in the art that arranging first area 12 and second area 16 so as to spell out words is not necessary, and in alternative embodiments of the present invention first area 12 and second area 16 may have any shape. For example, in FIG. 2, a panty shield 26 configured in accordance with the present invention is depicted where each one of first area 28 is of substantially circular shape and each one of second area 30 is substantially square shaped.

When used in a medical setting, it is imperative that there be substantially no leaching of indicator system components from the substrate to which the indicator system is attached. The attachment of indicators to a substrate is well within the ability of one skilled in the art. One family of chemical compounds that are suitable for use as a first indicator and a second indicator of the preferred embodiment of the present invention without leaching are indicators with negative functional groups. Suitable indicators include nitrazine yellow, thymol blue, bromthymol blue, xylenol blue, bromoxylenol blue, phenol red, m-cresol purple, chlorophenol red, bromcresol purple, alizarin, neutral red, and cresol red, see Table 1. A list of other suitable indicators can be found, for example, in U.S. Pat. No. 5,897,834. It is clear to one skilled in the art that the indicators specifically mentioned herein are just examples and any suitable indicators may be used. Further, there may be instances where the first indicator and/or the second indicator are made up of a combination of individual indicators.

Another non-limiting embodiment of the indicator system of the present invention is a secretion-monitoring article for the identification of vaginal infections such as bacterial vaginosis (BV) or parasitic. According to the present invention, an indicator system is made with a first indicator that indicates the presence of a fluid with a pH of around 4.7 to 7.0. The first indicator can be chosen, for example, from one or more of the group including nitrazine yellow, bromthymol blue and bromoxylenol blue. As can be seen in Table 1, these three indicators typically exhibit a bluish color when exposed to a fluid with a pH above 7.0. The second indicator can be chosen, for example, from the group including phenol red, thymol blue, xylenol blue and m-cresol purple. As can be seen in Table 1, upon exposure to a fluid with a pH above 8.0 these four indicators become red, blue, violet and violet, respectively. The reagent added to the second embodiment of the secretion-monitoring article of the present invention is, for example, urease.

As discussed hereinabove, urine of a healthy patient has a pH between 5.0 and 8.0. A patient having BV or parasite also has vaginal secretions with a pH between 4.7 and 6.5. If the liquid examined in the second embodiment of the secretion-monitoring article of the present invention is associated with BV or parasite, the first indicator changes color whereas the second indicator remains yellow. If the liquid examined contains urine, the first indicator changes color. Further, the urease reacts with the urine, producing ammonia, raising the pH of the fluid, and consequently causing the second indicator to change color.

The following examples set forth preferable embodiments of the present invention.

EXAMPLE 1

Reducing Erroneous Readings of Color-Changing Devices that Give an Indication of Elevated pH in the Vaginal Secretion The following example discloses the solution to produce an indicator that needs no color-table or scale to read results, that shows the user a stable indication for a few days, and that does not leach even when in contact with liquids for any practical length of time. For the non-invasive continuous monitoring version, the invention discloses a solution to avoid false positive readings due to urine contamination.

The device is a sticker or a pantyliner that contains two different indicator strips, embedded between layers of one-way absorbent tissues. The two indicators have a color transition-point at different pH levels. The color-reactions of the two indicators also have different reversibility in vaginal secretion Vs urine.

The first indicator strip changes color to stable blue, when sensing elevated pH in vaginal secretions (pH strip). The pH strip contains the pH indicator-Nitrazine-yellow, which has a pKa of 6.6 in aqueous solution, and with the innovative specific composition, changes the color when the vaginal secretion has a pH level of 5.0 or higher (the same innovative specific composition produces indicators for various pH levels, by using other negatively-charged members of the Ionizable phenol group).

The second strip is a control strip to detect urine (urine strip). The urine strip contains urease, an enzyme which hydrolyzes urea to ammonia, and a pH indicator m-Cresol purple which has a pKa of 8.2 in aqueous solution. When the strip is in contact with urine, the hydrolyzed ammonia raises the pH of the medium and the color of the m-Cresol purple changes from yellow to dark gray/green.

In a case where vaginal secretion with elevated pH (5.0–7.0) will reach the strips only the pH strip will change color and the change will remain stable for a few days.

Method of Preparation 1) pH Strip:

Step 1: To a 10 ml of Acetone add 150 mg Cellulose acetate, 107 µl Dibutylphthalate, 23 µl Aliquat, 150 µl 2-Ethoxy ethanol and 2.4 mg Nitrazine yellow dissolved in 150 µl DDW.

Step 2: Stir the mixture for few minutes to complete dissolving.

Step 3: Coat a polyester monofilament screening fabric with the polymer solution (coating other materials un-sensitive to acetone will produce various devices for various using instructions, with the same features).

2) Urine Strip:

First layer-step 1: To a 4.15 mL DDW add 45 mg PVP, 0.325 mL Urease/glycerol solution.

First layer-step 2: Coat a polyester monofilament screening fabric with the polymer solution.

First layer-step 3: The coated strips are dried-out over night at room temperature.

Second layer-step 1: To a 10 ml of THF add 150 mg Cellulose acetate, 107 µl Dibutylphthalate, 23 µl Aliquat, 150 µl 2-Ethoxy ethanol and 1.2 mg m-Cresol purple dissolved in 120 µl 1-Propanol.

Second layer-step 2: Stir the mixture for few minutes to complete dissolving.

Second layer-step 3: Coat the strip with the second polymer solution.

Second layer-step 4: After drying over night the wash the strip in a saline solution.

The device can be in the form of a swab with a tip produced in the same way as mentioned above, under the header: pH strip. The tip may be prepared by using a short strip, rolled on the stick of the swab, or by coating the tip of an integrated swab (implementing step 3), where the tip consists of any screening fabric.

EXAMPLE 2

A Device Able to Distinguish Accurately Between an Amniotic Fluid Leak or an Elevated pH Vaginal Discharged Secretion and Wetness Caused by Urine Incontinence Due to the severe consequences of amniotic fluid leakage, pregnant women undergo heavy stress and tend to seek for a health care provider upon any wet sensation in the area of the vagina. The common ways to checks for the presence of amniotic fluid are by examining the pH of vaginal secretions with pH indicators such as Nitrazine indicators, running the Fern-test or by visually identifying the source of the leakage.

Amniotic fluid has a pH level that varies between 6–8 and can be identified by a purple-blue color of a Nitrazine indicator. Since urine, has a pH level that varies between 5.0–8.0, measuring pH levels as a sole criterion can mislead to erroneous decisions. As the other two ways can be performed only in clinics and hospitals, and by trained staff, there is no practical solution for home monitoring.

In some situation, after amniocentesis tests and other occasions such as hi-risk pregnancies, there is a possibility of small amniotic leaks that can be detected only by continuous monitoring.

Current solutions and earlier inventions fail to serve as a home-use continuous monitoring device, as they leach in fluids, the color change is unstable, and the overlap between amniotic fluid pH level and the urine pH level misleads the users in as 30% of the cases.

The overlap of pH levels, between amniotic fluids and urine is also a great disadvantage for physicians treating patients with wet sensations. Providing pregnant women with a home-use continuous monitoring device, that distinguishes amniotic fluid leakage from urine incontinence with no false alarms, enabling the result reading at personal timing and discretion, and detects any small amniotic leak instantaneously, can on one hand help bring the user in-time to hospital when needed, and on the other hand avoid unnecessary hospitalization and concomitant patient stress.

Providing physicians with a reliable clinic instantaneous detecting article, that distinguishes amniotic fluid leakage from urine incontinence with no false alarms, can serve them by far better than available solutions today.

The article can be a sticker or a pantyliner with an embedded indicator strip. The strip contains the pH indicator-Nitrazine-yellow which has a pKa of 6.6 in aqueous solution.

Reaction of the indicator with amniotic fluid (pH 6–8) changes the color from yellow to stable dark blue. Reaction of the indicator with urine (pH 5–8) changes the color to fading green or fading turquoise. Urine with lower pH 5–5.5 doesn't change the indicator color.

The difference between the color reaction of the indicator with amniotic fluid and with urine consists of two parameters: the chemical composition of the fluids and the indicator's polymer chemical structure.

The following two equations demonstrates the different reactions

Equation 1:

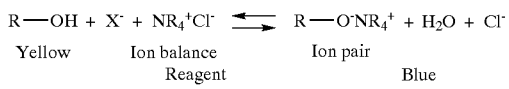

Equation 2:

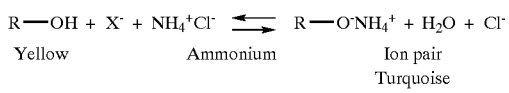

KEY:
X$^-$ = Base.
NR$_4^+$ = Ion balance reagent
R—O$^-$NR$_4^+$ = -phenolate-ion-balance reagent The ratio of ion-balance reagent versus indicator in the polymer matrix controls the transition point of the color and the color stability while drying. In the drying process the ion pair phenolate (the active site of the indicator)—ion-balance reagent is stable, which cause a stable performance of the color (equation 1—the relative concentration of the component doesn't change). In a different case where the concentration of the ion-balance reagent in the polymer is higher, the color of the indicator is getting dark while drying. The color darkening while drying is due to continuance deprotonation of the indicator's phenol by the basic excess of the ion balance reagent (equation 1—while drying the base concentration is getting high and the equilibrium turned to the right). The optimum molar ratio of ion-balance reagent to indicator is 10:1.

Ammonium ions in solution react like the ion-balance reagent and compete with the phenolate active site. While drying the ion pair phenolate—Ammonium hydrolyzed spontaneously to give the protonated yellow phenol (equation 2) while the phenolate—ion-balance reagent pair is stable (equation 1).

In a case where the medium contain ammonium ion the color changes govern by the relative concentration of the ion balance reagent in the polymer and the ammonium ion in the medium.

For example: in 100 mM buffer solution that contains 25 mM ammonium ion the concentration of the ammonium is in two orders of magnitude higher than the ion balance reagent in the polymer. These differences govern the turquoise color in solution and the fading color on drying.

Urine contains ammonium ions in concentration of 30–50 mM; amniotic fluid doesn't contain any substantial amount of ammonium ions, thus causing no fading influence as urine does.

Method of Preparation:

Step 1: To a 10 ml of Acetone add 150 mg Cellulose acetate, 107 µl Dibutylphthalate, 23 µl Aliquat, 150 µl 2-Ethoxy ethanol and 2.4 mg Nitrazine yellow dissolved in 150 µl DDW.

Step 2: Stir the mixture for few minutes to complete dissolving.

Step 3: Coat a polyester monofilament screening fabric with the polymer solution to give the desired product.

The device can be a swab with a tip produced in the same way as mentioned above, under the header: pH strip. The tip may be prepared by using a short strip, rolled on the stick of the swab, or by coating the tip of an integrated swab (implementing step 3), where the tip consists of any screening fabric.

EXAMPLE 3

A Device Able to Distinguish Accurately Between Normal Urine and Infected Urine

The reoccurrence of urinary tract infections in certain patients present the need to quickly and easily diagnose whether the patient has another urinary tract infection. Presently, to determine if a patient has a urinary tract infection they must make an appointment to visit a doctor. Furthermore, if the patient is susceptible to the reoccurrence of urinary tract infections they must make periodic visits to the doctor's office to ensure that the infection has not reoccurred. Having a device that would allow the user to determine if they had a urinary tract infection again would minimize stress and time consumed by visits to the doctors office and result in quicker diagnosis of the infection, resulting in a reduction in pain suffered by the patient and a more timely treatment of the infection.

The article in this example is a diaper or a panty liner with an indicator that can distinguish between normal urine and infected urine. The user wears the article so that urine can come in contact with the article. The reaction of the indicator with urine (pH 5–8) changes the color from yellow to green or turquoise. The drying process of the indicator strip at room temperature is short (5 minutes). When normal urine comes in contact with the indicator strip the color changes fade while drying. The color change is completely reversible and the strip becomes yellow again. On the other hand when infected urine comes in contact with the indicator strip the color changes to green or turquoise and stay constant while drying.

The reversibility of the color changes depends on two different factors of the environment:

1. Chemical environment:
    a. The pH level of the fluid—pH level higher than the pKa gives a stable color change.
    b. Buffer capacity of the solution—Explained extensively in EXAMPLE 4.
    c. Ammonium salts content in the solution—explained extensively in EXAMPLE 2.
2. Biological environment:
    a. Protein presence in urine gives a stable color change and the reaction is not reversible.

Infected urine provides a stable color change to the indicator, which color change is not reversible. Furthermore, bacteria presence in vaginal secretion fluid also gives a stable color change so that the color change is not reversible.

EXAMPLE 4

A Device Able to Distinguish Between Bacterial or Parasitic Infected Secretions and Normal or Candida Vaginal Secretions. Advantageous Attributes of Polymer Matrix Compared to Commercially Available pH Indicator Paper The buffering capacity of vaginal secretions was studied. In view of these findings the chemical attributes of the polymer matrix of the invention compared to commercially available pH indicator paper were also studied. It was determined that because of the high quantity of homogenous secretions typical of BV, that vaginal secretion associated with BV have a low buffer capacity due to transudation of extracellular fluid.

Bacterial vaginosis (BV) is characterized by production of increased quantities of malodorous vaginal discharge. The vaginal discharge of women with BV is described as being thin (low viscosity), off-white-gray (milk-like consistency), and homogeneous (distinctly not curd-like).

In the vagina there are no glands so that the fluid which it contain results from cervical secretion, vulvar secretions from sebaceous, sweat, Bartholin and Skene glands, exfoliated cells, endometrial and oviductal fluids but mainly from liquid transudation through the vaginal epithelial walls.

As mentioned above, one of the characteristic of BV is the homogeneous discharge. A women having BV typically has an increase in the discharge amount. The source of this liquid is extracellular fluid (interstitial fluid) that surrounds the epithelial cells in the vagina wall.

The ionic composition of the extracellular fluid and the plasma is quit similar with some differences reflecting the inability of large solutes, like proteins, to cross the cells wall.

A decrease in protein levels and other large organic molecules and the increase of water content in BV secretions lowers the buffering capacity of the secretions. Thus, secretions associated with BV have a lower buffer capacity than healthy vaginal secretions.

Experimental and Results

Polymer Color Change in Solution:

100 mM buffer phosphate citrate was prepared with seven different pH values. Each buffer was diluted to four different concentrations: 50, 20, 10 and 5 mM and the pH was adjusted using NaOH 1M or HCl 1M. A Nitrazine polymer matrix of the invention was dipped in each buffer and the change in color was noted and represented by a numeric values as follows: 0=Yellow; 1=Light Green; 2=Green; 3=Dark green. The results are summarized in Table 2 and FIG. 6.

TABLE 2

Color change of polymer mixture dependent on pH

| pH (±0.05) | 100 mM | 50 mM | 20 mM | 10 mM | 5 mM |
|---|---|---|---|---|---|
| 4.0 | 0 | 0 | 0 | 0 | 0 |
| 4.3 | 0 | 0 | 0 | 0 | 1 |
| 4.5 | 0 | 0 | 0 | 1 | 1 |
| 4.7 | 0 | 0 | 1 | 1 | 2 |
| 5.0 | 1 | 1 | 1 | 2 | 2 |
| 5.2 | 1 | 1 | 2 | 2 | 2 |
| 5.5 | 2 | 2 | 3 | 3 | 3 |

*Color scale conversion: 0—Yellow; 1—Light Green; 2—Green; 3—Dark green;

A follow-up experiment was done using commercially available Nitrazine Paper (APOTHECON Inc., Princeton, N.J.) with the same regime of pH buffer solutions. The Nitrazine Paper did not significantly change color in any of the pH buffer solutions. The results indicated that the commercially available Nitrazine Paper sensitivity was insufficient to indicate a color change significant enough to distinguish and identify the difference in pH of any of the measured solutions.

It is known that Nitrazine yellow is a weak acid pH indicator, which when dissolved in water dissociate slightly and form the conjugate base.

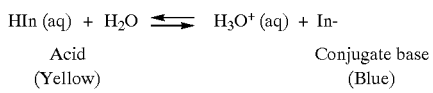

$$\text{HIn (aq)} + \text{H}_2\text{O} \rightleftharpoons \text{H}_3\text{O}^+ \text{(aq)} + \text{In-}$$

Acid                   Conjugate base
(Yellow)              (Blue)

Figure 6:
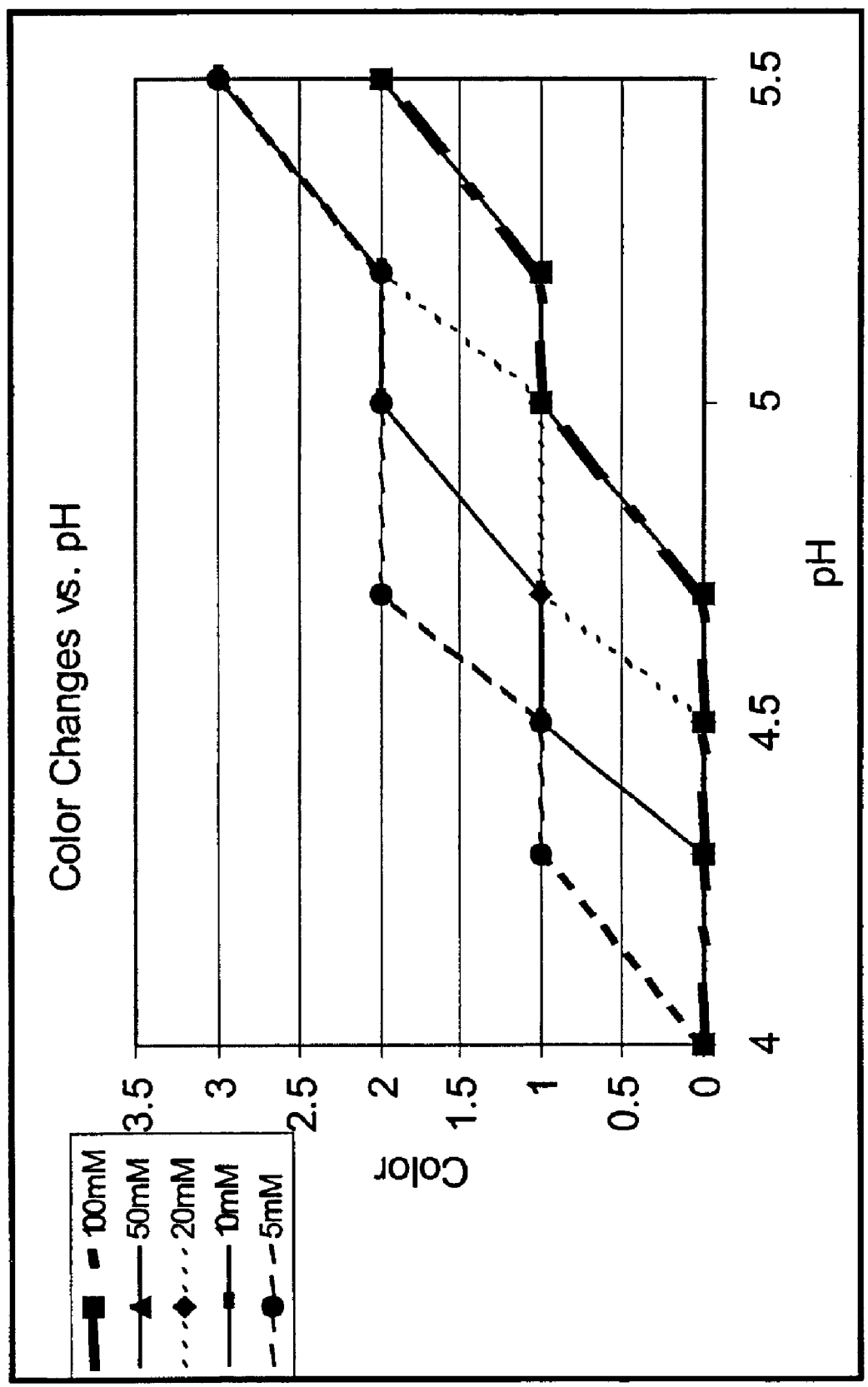
FIG. 6 is a graph showing the change in color of the polymer vs. the change in pH, wherein the color scale conversion is as follows: 0-Yellow; 1-Light Green; 2-Green; 3-Dark green.

It is clear from the results (Table 2; FIG. 6) that when the buffer capacity of the solution is lower the color change occurs at a lower pH. The variation between the first color change in the 5 mM buffer solution is approximately 0.7 pH units lower than the first color change of the 50 mM buffer solution.

This is achieved in our polymer matrix indicator because of its unique formulation. The Nitrazine yellow environment in the polymer matrix is hydrophobic, composed of electronic neutral organic substrate except of the ion balance reagent that does not contribute to the acid-base balance. In contrast, the chemical composition of the commercial Nitrazine Paper is a hydrophilic formulation that contains some degree of ionic buffer.

The mechanism of the color changes of the polymer matrix is described in the following equation:

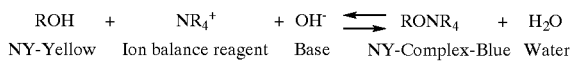

$$\text{ROH} + \text{NR}_4^+ + \text{OH}^- \rightleftharpoons \text{RONR}_4 + \text{H}_2\text{O}$$

NY-Yellow    Ion balance reagent    Base    NY-Complex-Blue    Water

The reaction is in equilibrium and the color of the polymer depends on the ratio of free NY compared to the NY complex.

In solution the color change is governed by the pH and the buffer capacity.

On the drying process of the polymer matrix the NY complex dissociate easily when the buffering system is highly concentrated or when there is high concentration of protonated cations like NH4+ in urine. The dissociation of the complex accurse due to the basic nature of the phenolate ion in the NY complex and the high concentration of protons compare to the Ion balance reagent. The dissociation of the complex express in color changes from green or blue to the yellow one. On the other hand when the buffer is weak or the medium is highly watery the NY-complex stay stable at any color including the light green one. The stability of the color is due to the lack of protons compared to the Ion balance reagent concentration.

Assessment of Buffer Capacity of Vaginal Secretion:

In order to examine the buffer capacity of vaginal secretions, different buffer solutions were titrated with 0.1 N NaOH in comparison with vaginal secretions.

Figure 7:
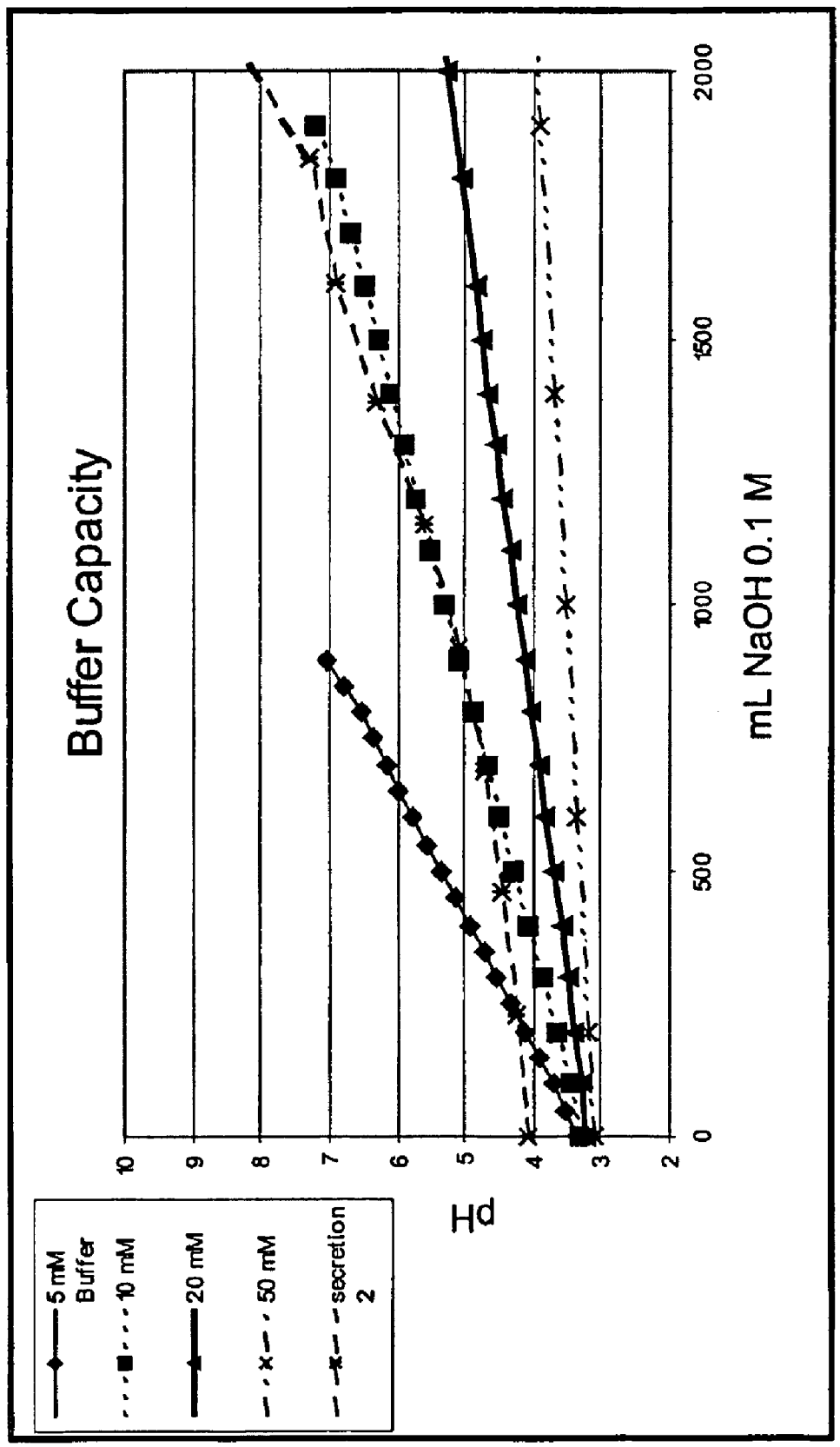
FIG. 7 is a graph demonstrating the buffering capacity of vaginal secretions. The graph compares the pH of the butter or secretion being titrated to the mL NaOH 0.1 M added.

The vaginal secretions were collected with a sterile swab. The sterile swab was weighted on an analytical balance before and after secretion sampling. The secretion was then diluted in ddH$_2$O and titrated as the other buffer solutions with NaOH 0.1M. The dilution factor was taken in account in determining the buffer capacity of the vaginal secretion. The results of the titrations are summarized in FIG. 7.

This study validates that the nature of color changes of our polymer matrix has an advantage compare to commercial Nitrazine paper or devices based on Nitrazine paper in detecting infection which has low buffer capacity characteristics. For example infected vaginal secretion with pH levels of 4.3–4.9 with low buffer capacity will be detected by our polymer while commercial Nitrazine paper will fail to notice it.

Improved Methods for Attaching Indicators to a Substrate

Details and variations concerning the method of manufacture of a secretion-monitoring article for implementing the indicator system of the present invention or applying the method of the present invention are well described in the prior art.

As described hereinabove, U.S. Pat. No. 5,897,834 describes a solid pre-formed polymer to which quaternary ammonium groups are covalently bound. Negatively charged indicators are non-covalently bound to the polymer. The non-covalent bonds are strong enough so that the attached indicators do not leach out in an aqueous solution. In addition, the indicators bound to the polymer have a sharpened pH color transition, allowing an accurate determination of the pH of the applied fluid. The polymer can be applied to various substrates. However, indicators bound to these polymers are less useful in non-clinical settings as the indicated pH of vaginal secretions after drying is lower than that of fresh vaginal secretions, leading to a false positive results.

In the present invention is disclosed a method suitable for attaching indicators to a substrate so that the indicators do not leach out in an aqueous fluid. Especially suitable indicators are those with a negatively charged group, such as those listed in Table 1 or, for example, in U.S. Pat. No. 5,897,834. The polymer of the present invention is exceptionally suited for attaching the indicator system of the present invention to a substrate. Further, experiments show that unlike other methods and polymers known in the art, changes in color of indicator attached according to the methods of the present invention are fast. The color is retained over a long period of time and even when the applied liquid dries. Repeated cycles of drying and wetting also do not change the color. Thus, in practical terms, there is time for a user to get to a health care professional without the color of the indicator changing.

Application of Indicator to a Substrate

In a first embodiment of a method of attaching an indicator to a substrate according to the present invention, an indicator is mixed with a preformed polymer in a suitable solution and then applied to a substrate.

In more detail, a polymer solution is prepared containing dry pre-formed polymer, plasticizer, a wetting agent, an ion-balance reagent, a solvent and an indicator. When practicing the method of the present invention, a reagent as described is also added.

The preformed polymer can be selected from various preformed polymers, although cellulose polymers such as nitrocellulose, cellulose acetate or ethyl cellulose are preferred. The preformed polymer makes up 20% to 50% of the weight of the solution. Preferred is that the polymer makes up 25% to 45% of the solution, more preferred is that the polymer makes up 30% to 43% of the solution, and most preferred is that the polymer makes up 36% to 39% by weight of the solution. As is clear to one skilled in the art, it is also possible to use a combination of suitable preformed polymers when making one polymer solution.

Although any suitable plasticizer can be used, bis-(2-butoxyethyl) adipate (BBPA, CAS 141-18-4), bis-(2-ethylhexyl) sebacate (DOS, CAS 122-62-3), diethyl phthalate (DEP, CAS 84-66-2) or dibutyl phthalate (DBP, CAS 84-74-2) are preferred. The plasticizer makes up 15% to 40% of the weight of the solution. Preferred is that the plasticizer makes up 20% to 35% of the solution, more preferred is that the plasticizer makes up 25% to 31% of the solution, and most preferred is that the plasticizer makes up 27% to 29% by weight of the solution. As is clear to one skilled in the art, it is also possible to use a combination of suitable plasticizers when making one polymer solution.

Although any suitable wetting agent can be used, triethylene glycol, ethylene glycol, sorbitol or 2-ethoxy ethanol are preferred. The wetting agent makes up 15% to 45% of the weight of the solution. Preferred is that the wetting agent makes up 21% to 40% of the solution, more preferred is that the wetting agent makes up 26% to 34% of the solution, and most preferred is that the wetting agent makes up 29% to 31% by weight of the solution. As is clear to one skilled in the art, it is also possible to use a combination of suitable wetting agents when making one polymer solution.

Although any suitable ion-balance reagent can be used, tricaprylylmethyl ammonium chloride (Aliquat 336, CAS 5137-55-3), tridodecylmethyl ammonium chloride (TDMAC. CAS 7173-54-8) or cetyltimethyl ammonium chloride (CTAC, CAS 112-02-7) are preferred. The ion-balance reagent makes up 0.1% to 10% of the weight of the solution. Preferred is that the ion-balance reagent makes up 1% to 8% of the solution, more preferred is that the ion-balance reagent makes up 3% to 7% of the solution, and most preferred is that the ion-balance reagent makes up 4% to 6% by weight of the solution. As is clear to one skilled in the art, it is also possible to use a combination of suitable ion-balance reagents when making one polymer solution.

The components of the solution are added so that the sum of weights of pre-formed polymer, plasticizer, wetting agent and ion-balance reagent is equal to 100%.

The desired indicator is added to the solution. Although any suitable indicator can be used, it is preferred that the indicator molecules have a negatively charged functional group such as acetate or sulfonate. Most preferably, the indicators used, separately or in combination, are chosen from amongst indicators listed in Table 1 and in U.S. Pat. No. 5,897,834. The total amount of indicator added is 0.05% to 5% of the weight of the polymer solution as described above. Preferred is that the indicator is 0.05% to 3% of the polymer solution, more preferred is that the indicator is 0.1% to 1% of the polymer solution, and most preferred is that the indicator is 0.2% to 0.4% of weight of the polymer solution.

When it is desired to add a reagent in preparation of the indicator system of the present invention, reagent is added to the polymer solution. For example, when urease is used, any suitable amount of urease can be added although it is preferred that the concentration of urease is about 10 units for each 0.01%–0.1% of indicator added to the polymer solution.

Further, an amount of solvent is added that is suitable for making any easily applied solution/indicator mixture. Typically, 150 mg of polymer solution is dissolved in between 1 ml and 30 ml of solvent, preferably between 5 ml and 15 ml solvent. Although any suitable solvent or mixture of solvents may be used, preferred are ethyl acetate or substantially volatile ethers such as diethyl ether, isopropyl ether, t-butyl methyl methyl ether or tetrahydrofuran Once the mixture is ready, it is applied by suitable means to the substrate. Application can be done, for example, by spraying or spreading the mixture on the substrate, or by dipping the substrate in the mixture. The substrate can be of many suitable materials known in the art such as polyester membranes, polypropylene membranes, cellulose membranes, paper, cotton or linen. The structure of the substrate may be, for example, a fiber, a mesh, gauze, a fabric or a membrane. The solvent of the mixture is allowed to evaporate. Once the mixture dries onto the substrate, the substrate is integrated into whatever secretion-monitoring article is desired, such as a panty shield.

As is clear to one skilled in the art that when the indicator system of the present invention is implemented, a first mixture with a first indicator is made, and a second mixture with a second indicator and a reagent is made, both mixtures as described hereinabove. Each of the two mixtures is applied to area on the substrate, as described hereinabove. Preferably the area of application of the first mixture is substantially distinct from the area of application of the second mixture.

In certain applications, the liquid to be tested may contain biological polymers such as proteins or fats. For example, amniotic fluid and urine often contain proteins. The biological polymers may plug up the pores in the substrate reducing the effectivity of the testing method. This can be exceptionally significant in panty shield applications such as panty shield 32 depicted in FIG. 3. In such a case, it is preferable to interpose a microporous membrane 34, such as a dialysis membrane (e.g., cellulose membrane, catalog nr. D-9402, Sigma-Aldrich, St. Louis Mo.), between indicator substrate 36 and a source 38 of secretion 40. Large-sized materials 42 in secretion 40 cannot penetrate microporous membrane 34 whereas fluid component 44 of secretion 40 penetrates microporous membrane 34 to react with indicator substrate 36. Panty shield 32 in FIG. 3 further includes two side flaps 46 (only one is visible in FIG. 3) configured to allow attachment of panty shield 32 to an undergarment of a user, in such a way keeping panty shield 32 in the proximity of the vagina of a user.

In a second embodiment of a method of attaching an indicator to a substrate according to the present invention, a substrate is first treated with a surfactant solution. After the solution dries, an indicator solution is applied to the substrate. The substrate can then be integrated into a product.

Although any surfactant can be used, when it is desired to attach negatively charged indicators to a neutral substrate, a surfactant with a cationic functional group is used, preferably Aliquat 336, TDMAC or CTAC. Although any suitable solvent or mixture of solvents may be used, preferred are ethyl acetate or substantially volatile ethers such as diethyl ether, isopropyl ether, t-butyl methyl ether or tetrahydrofuran. The surfactant is dissolved in the solvent at any suitable concentration. Preferred is that the surfactant makes up 0.01% to 2% of the solution, more preferred is that the surfactant makes up 0.1% to 0.5% of the solution, and most preferred is that the surfactant makes up 0.15% to 0.25% by weight of the solution. As is clear to one skilled in the art, it is also possible to use a combination of suitable surfactants. The surfactant solution is applied to the substrate. Application is done, for example, by spraying or spreading the mixture on the substrate, or by dipping the substrate in the mixture. The substrate can be of many suitable materials known in the art such as polyester membranes, polypropylene membranes, cellulose membranes, paper, cotton or linen. The structure of the substrate may be, for example, a fiber, a mesh, gauze, a fabric or a membrane. The solvent of the surfactant solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

After the solvent of the surfactant solution has evaporated, an indicator solution is applied to the substrate. Although any solvent or mixture of solvents may be used, preferred are ethyl acetate or substantially volatile ethers such as diethyl ether, isopropyl ether, t-butyl methyl ether, or tetrahydrofuran. Although any suitable indicator can be used, it is preferred that the indicator molecules have a negatively charged functional group such as acetate or sulfonate when the surfactant used is a cationic surfactant. Most preferably, the indicators used, separately or in combination are chosen from amongst those listed in Table 1 or, for example, in U.S. Pat. No. 5,897,834. The amount of indicator added is 0.00001% to 1% of the weight of the indicator solution as described above. Preferred is that the indicator is 0.0001% to 0.1% of the indicator solution, more preferred is that the indicator is 0.001% to 0.01% of the indicator solution, and most preferred is that the indicator is 0.002% to 0.004% of weight of the indicator solution.

When it is desired to add a reagent in preparation of the indicator system of the present invention, reagent is added to the indicator solution. For example, when urease is used, any suitable amount of urease can be added. Although any suitable concentration of urease can be used, preferred is a concentration of between 1 and 100 unit/ml. More preferred is a concentration of 2 and 50 unit/ml and even more preferred a concentration of 5 and 20 unit/ml.

In an additional embodiment of the present invention, a reagent solution is prepared separately from the indicator solution. When urease is used as a reagent, any suitable concentration of urease can be used. It is preferred that a concentration of between 1 and 100 unit/ml urease be used, more preferred is a concentration of 2 and 50 unit/ml and even more preferred a concentration of 5 and 20 unit/ml.

The indicator solution (or indicator/reagent solution) is applied to the substrate. Application can be done, for example, by spraying or spreading the indicator solution on the substrate, or by dipping the substrate in the indicator solution. The solvent of the indicator solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

When a reagent solution is prepared separately from the indicator solution, the reagent solution is applied in substantially the same way as described hereinabove, either before or after application of the indicator solution.

Irrespective of the exact concentration of the indicator solution and of the surfactant solution used, it is preferable to apply an amount of each one of the solutions so that the molar concentration of surfactant applied per unit area of substrate is roughly one hundred times greater than the molar concentration of indicator applied per unit area of substrate. The indicator solution is applied to the substrate to areas where surfactant was previously applied.

As is clear to one skilled in the art, when the indicator system of the present invention is implemented, a first solution with a first indicator is made, and a second solution with a second indicator and a reagent is made, both solutions as described hereinabove. Each of the two solutions is applied in distinct areas on the substrate, as described hereinabove.

EXAMPLE 5

Solution A: 370 mg cellulose acetate, 280 mg DBP, 150 mg sorbitol, 150 mg 2-ethoxyethanol, 50 mg TDMAC wee combined. 3 mg Bromthymol blue were added, 20 ml THF were added. The solution was vigorously stirred.

Solution B: 370 mg cellulose acetate, 280 mg BBPA, 300 mg ethylene glycol, 50 mg TDMAC were combined. 3 mg m-cresol purple and 30 units urease were added. 20 ml 20 THF were added. The solution was vigorously stirred.

1a. Cotton gauze was dipped in Solution A. When the solution dried, the cotton gauze was cut in half. The first half was dipped in a pH 7 test solution. The first half became purple. The first half was allowed to dry in ambient conditions, with no substantial change of color. After three hours, the second half was dipped in a pH 7 test solution. The second half became purple. The colors of the first half and of the second half were substantially the same.

1b. Cotton gauze was dipped in Solution B. When the solution dried, the cotton gauze was cut in half. The first half was dipped in urine. The first half became violet. The first half was allowed to dry in ambient conditions, with no substantial change of color. After three hours, the second half was dipped in urine. The second half became violet. The colors of the first half and of the second half were substantially the same.

1c. Solution A and Solution B were applied in alternating stripes on cotton gauze at a density of about 50 ul/mm2. Amniotic fluid was applied to the gauze, changing the color of the stripes of Solution A to purple. Urine was applied to the gauze, changing the color of the stripes of Solution B to violet. The gauze was allowed to dry at ambient conditions for three hours and cut in half. Urine was applied to the first half. The colors of the stripes in the first half and the second half of the gauze were substantially the same.

EXAMPLE 6

Three solutions were prepared:

Solution A: 0.2% Aliquot 336 in DDW (double distilled water);

Solution B: 10 unit/ml urease and 0.003% m-cresol purple in DDW; and

Solution C: 0.003% nitrazine yellow in isopropyl ether.

A nitrocellulose membrane was dipped in Solution A and transferred to an atmosphere of 50 mm Hg. After 30 minutes, the membrane was removed from the vacuum. Solution B was applied in a pattern resembling the word "NO" at a density of 50 μl/mm2. Solution C was applied in a pattern resembling the word "AMNIO" at a density of 50 μl/mm2. The membrane was transferred to an atmosphere of 50 mm Hg. After 30 minutes, the membrane was removed from the vacuum. The membrane was dipped in a pH 7 test solution. The word AMNIO appeared in purple. After drying at ambient conditions for three hours, no substantial change of color was observed. The membrane was dipped in urine. The word NO appeared in violet.

It is clear to one skilled in the art that the present invention is not limited to the embodiments described herein but also relates to many types of conventional modifications thereof, which are within the scope of the claims.

Method of Constructing the Article

Figure 4A:
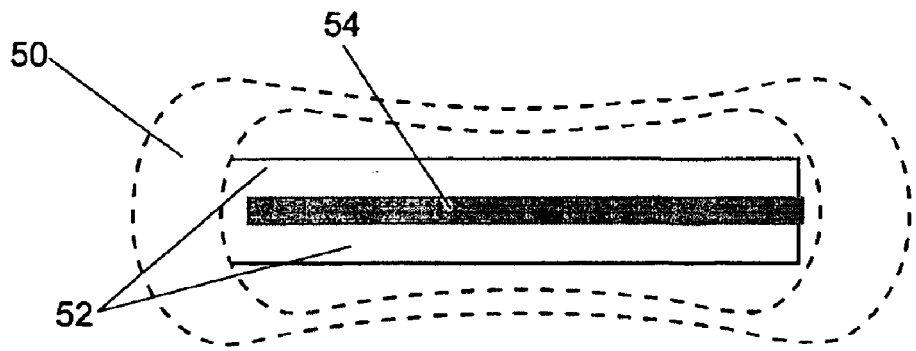
FIG. 4A–C are schematic top views of an embodiment of the secretion-monitoring article with two pH indicators.
Figure 4B:
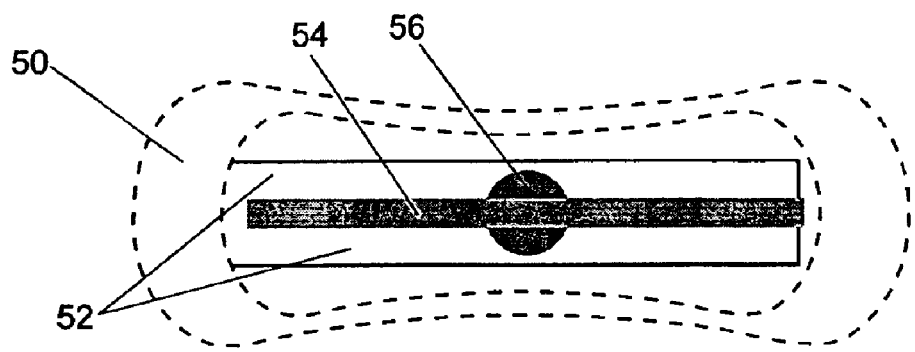
Figure 4C:
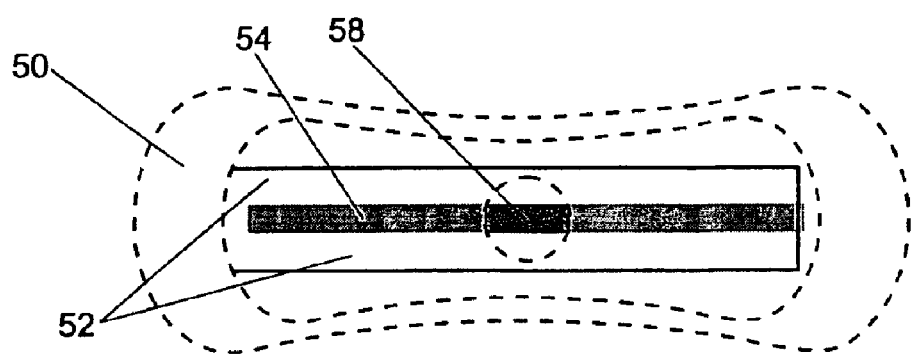

FIGS. 4A–C and 5A–B provide visual examples of two methods non-limiting examples of constructing the article. FIGS. 4A–C show an article in the form of a panty shield 50 constructed with two indicators 52 and 54. In FIG. 4A, the panty shield 50 is constructed with a pH indicator 52 for detecting normal biological fluids and a second pH indicator with high pH dye and a reagent, such as urease, for detecting interfering biological fluids, such as urine. FIG. 4B depicts the panty shield 50 wherein a normal fluid, without an interfering fluid, changes the color 56 of the pH indicator 52. In contrast, FIG. 4C depicts the panty shield 50, wherein an interfering biological fluid, such as urine, changes the color 58 of the second pH indicator 54.

Figure 5A:
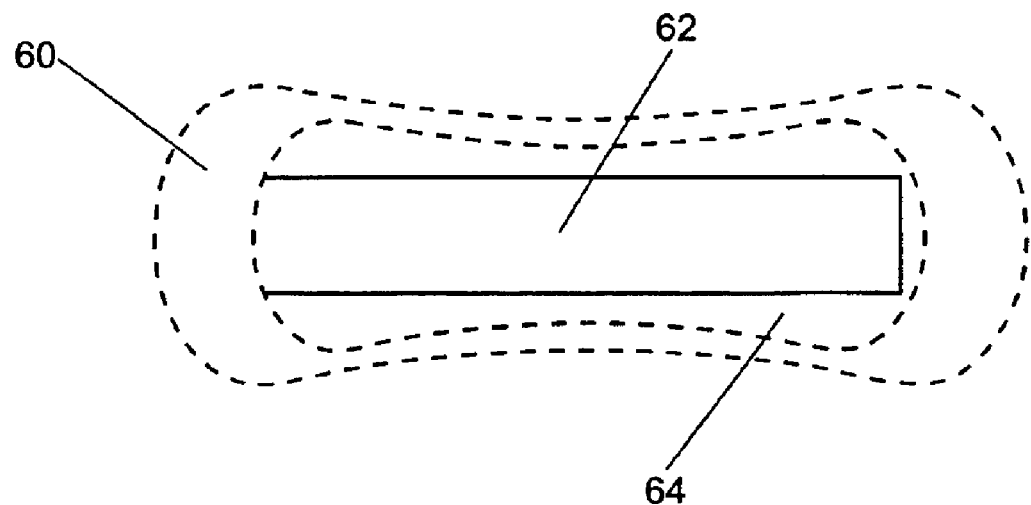
FIGS. 5A–B are schematic top views of an embodiment of the secretion-monitoring article with one pH indicator device that can distinguish between urine and other body fluids, such as amniotic fluid.
Figure 5B:
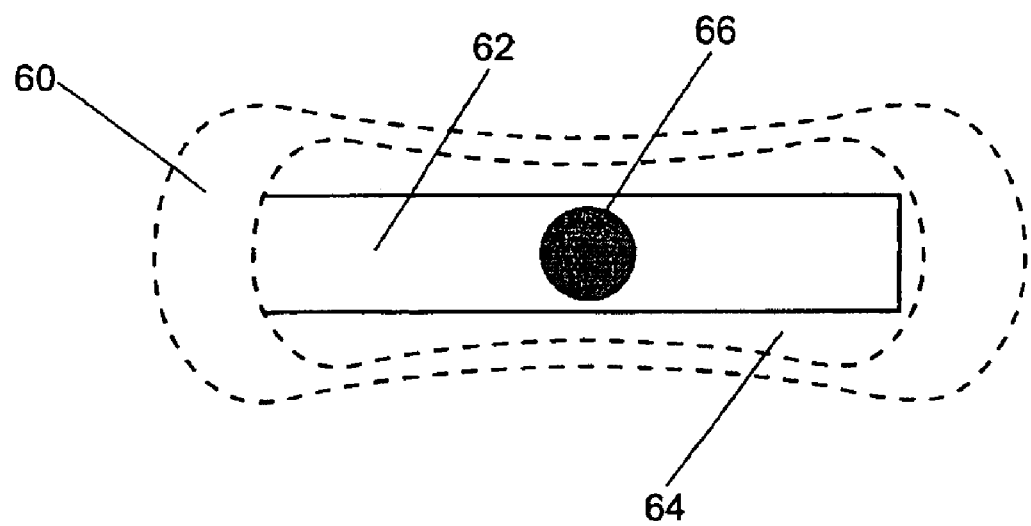

In a separate embodiment, the article can be made with only a single indicator as shown in FIGS. 5A and 5B. FIG. 5A depicts the article in the form of a panty shield 60, comprising a sticker 64, with an indicator 62 constructed so as not to react with an interfering biological fluid like urine. When a biological fluid to be detected comes in contact with the indicator, as show in FIG. 5B, the indicator changes color 66, whereas if the indicator comes in contact with urine it will not change colors.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention. Thus the expressions "means to . . . " and "means for . . . ," or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A secretion-monitoring article for identifying a secreted biological fluid comprising: a body that includes an absorbent material for absorbing a biological fluid secreted from a person, and an indicator system that has at least one pH determining member that includes a chemical composition that reacts with fluids that contain urea differently than with fluids that do not contain urea and in a manner such that fluids that contain urea can be distinguished from fluids that do not contain urea while avoiding false positive indications for both fluids, the pH determining member further comprising a hydrophobic chemical composition that reacts with fluids based on the buffer capacity of the fluid, such that fluids having different buffer capacities can be distinguished, wherein the indicator system is associated with the absorbent material such that the biological fluid contacts the indicator system to identify the secreted biological fluid.

2. The article of claim 1, wherein the pH determining member records a pH change after coming in contact with the biological fluid and is resistant to further change due to long use or wetting and drying cycles.

3. The article of claim 1, further comprising a plurality of pH determining members.

4. The article of claim 1, further comprising mounting means for placing the absorbent body in a position to receive biological fluids secreted from the person.

5. The article of claim 1, wherein the absorbent material of the body is a swab, gauze, panty shield, hygienic napkin, a diaper or interlabial absorbent structure.

6. The article of claim 1, wherein the pH determining member changes color when contacted by a vaginal secretion having a pH level associated with vaginosis or amniotic fluid leakage without fading upon drying, but the color change fades upon drying when contacted by urine.

7. The article of claim 1, wherein the pH determining member changes color when contacted by a vaginal secretion having a pH level associated with vaginosis or amniotic fluid leakage without fading upon drying, but the color change drifts to another color upon drying when contacted by urine.

8. The article of claim 1, wherein the pH determining member comprises polyester membrane.

9. The article of claim 1, wherein the article is in the form of a pantyliner.

10. A secretion-monitoring article for identifying a secreted biological fluid comprising: a body that includes an absorbent material for absorbing a biological fluid secreted from a person, and an indicator system that has at least one pH determining member having a hydrophobic chemical composition that contains a quaternary amine, the pH determining member changing color when contacted by a biological fluid having a pH associated with vaginosis or amniotic fluid wherein the reaction of the composition with fluids containing urine is a reversible color change, while the reaction of the composition with fluids that do not contain urine is stable.

11. The article of claim 10, wherein the article comprises a polyester screening fabric.

12. The article of claim 10, wherein the article is in the form of a pantyliner.

13. A secretion-monitoring article for the identification of infected urine comprising: a body that includes an absorbent material for absorbing urine from a person and an indicator system that has at least one indicator having a chemical composition that reacts with normal urine differently than infected urine, wherein the indicator changes colors when contacted by urine, the color change being irreversible when contacted by infected urine, while the color change is reversible when contacted by normal urine, the indicator system being associated with the absorbent material such that the urine contacts the indicator system.

14. The article of claim 13, further comprising a mounting means for placing the absorbent body in a position to receive the urine secreted from the person.

15. The article of claim 13, wherein the absorbent material of the body is a swab, gauze, panty shield, hygienic napkin, a diaper or interlabial absorbent structure.

16. The article of claim 13, wherein the color change fades or drifts to another color upon drying if the urine is not infected.

17. A secretion-monitoring article for the identification of bacterial or parasitic infected vaginal secretions comprising: a body that includes an absorbent material for absorbing vaginal secretions and an indicator system that has at least one indicator comprising a hydrophobic chemical composition that reacts with low buffer capacity secretions differently than with high buffer capacity secretions and in a manner such that low buffer capacity secretions can be distinguished from high buffer capacity secretions while avoiding false positive indications for both, wherein the indicator changes colors when contacted by a vaginal secretion, the color change is stable when contacted by a bacterial or parasitic infected vaginal secretion, but the color change is reversible when contacted by a normal or candida vaginal secretion.

18. The article of claim 17, wherein the indicator reacts with normal or candida vaginal secretions differently than bacterially or parasitic infected vaginal secretions, wherein the indicator changes color when contacted by bacterially or parasitic infected vaginal secretion and the indicator system is associated with the absorbent material such that the vaginal secretions contact the indicator system to identify bacterial or parasitic infections.

19. The article of claim 17, further comprising a mounting means for placing the absorbent body in a position to receive vaginal secretions from the person.

20. The article of claim 17, wherein the absorbent material of the body is a swab, gauze, panty shield, hygienic napkin, a diaper or interlabial absorbent structure.

21. The article of claim 17, wherein the color change fades upon drying when contacted by normal or candida vaginal secretions, but not bacterial or parasitic infected vaginal secretions.

22. The article of claim 17, wherein the color change drifts to another color upon drying when contacted by normal or candida vaginal secretions, but not bacterial or parasitic infected vaginal secretions.

23. The article of claim 17, wherein the article comprises a polyester screening fabric.

24. The article of claim 17, wherein the article is in the form of a pantyliner.

25. A diagnostic device for detection of vaginosis or amniotic fluid leakage without giving a false positive result due to contact with an interfering biological secretion, the device comprising:

a substrate, and an indicator system being attached to the substrate, the indicator system including:

a first indicator attached to the substrate in one or more first areas;

a second indicator attached to the substrate in one or more second areas; and a reagent attached to the substrate in the one or more second areas, wherein the first indicator changes color when contacted by a vaginal secretion having a pH level associated with vaginosis or amniotic fluid leakage and the second indicator changes color when contacted by an interfering biological secretion reacting with the reagent, but the second indicator does not change color when contacted by vaginal secretions having a pH level associated with vaginosis or amniotic fluid leakage.

26. The device of claim 25, wherein the substrate, first pH indicator and the second indicator are configured so that a color attained upon a color transition remains unchanged three hours after drying.

27. The device of claim 25, further comprising an absorbent body in contact with the substrate so that the substrate is wet by fluids absorbed by the absorbent body.

28. The device of claim 27, wherein the vaginal secretion absorbed by the absorbent body passes through a microporous membrane prior to absorption by the absorbent body.

29. The device of claim 27, further comprising a mounting means for placing the absorbent body in a position to receive the vaginal secretion.

30. The device of claim 25, wherein the reagent is urease.

31. A secretion-monitoring article for identifying a secreted biological fluid comprising: a body that includes an absorbent material for absorbing a biological fluid secreted from a person, and an indicator system that has at least one pH determining member comprising a hydrophobic chemical composition that contains a quaternary amine, the pH determining member changing color when contacted by urine or a biological fluid having a pH associated with bacterial vaginosis or amniotic fluid, wherein the reaction of the composition with urine is a reversible color change, while the reaction of the composition with fluids associated with bacterial vaginosis or amniotic fluid is stable.

32. The article of claim 31, wherein the color change fades or drifts to another upon drying when contacted by urine, but not when contacted by fluids associated with bacterial vaginosis or amniotic fluid.

33. The article of claim 31, wherein the pH determining member comprises a polyester membrane.

34. The article of claim 31, wherein the article is in the form of a pantyliner.

* * * * *

UNITED STATES PATENT AND TRADEMARK OFFICE
CERTIFICATE OF CORRECTION

PATENT NO.    : 6,921,647 B2
DATED         : July 26, 2005
INVENTOR(S)   : Kritzman et al.

It is certified that error appears in the above-identified patent and that said Letters Patent is hereby corrected as shown below:

Column 22,
Lines 18-19, change "to receive biological fluids secreted" to -- to receive the biological fluid secreted --.

Signed and Sealed this

Thirteenth Day of September, 2005

JON W. DUDAS
*Director of the United States Patent and Trademark Office*